United States Patent
Toennesland et al.

(10) Patent No.: US 6,648,289 B2
(45) Date of Patent: Nov. 18, 2003

(54) MECHANISM FOR HORIZONTAL ADJUSTABILITY OF OPERATOR PANEL ON SCANNER

(75) Inventors: Aasulv Toennesland, Hornnes (NO); Louis Morasse, Bromont (CA); Robert A. Meurer, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1 day.

(21) Appl. No.: 09/919,159

(22) Filed: Jul. 31, 2001

(65) Prior Publication Data

US 2003/0025054 A1 Feb. 6, 2003

(51) Int. Cl.$^7$ ................................................. E04G 3/00
(52) U.S. Cl. ...................... 248/276.1; 248/591; 248/131
(58) Field of Search ............................ 403/64, 83, 65, 403/98, 84; 312/208.1; 108/93, 94, 137; 248/276.1, 918, 920, 282.1, 591, 131, 186.2

(56) References Cited

U.S. PATENT DOCUMENTS 4,890,561 A * 1/1990 Hampshire et al. ......... 108/137
5,339,749 A * 8/1994 Hirose ........................ 108/143
5,611,551 A * 3/1997 Lin ............................. 280/32.5

* cited by examiner

Primary Examiner—Kimberly Wood
(74) Attorney, Agent, or Firm—Ostrager Chong & Flaherty LLP

(57) ABSTRACT

A mechanism which achieves positional flexibility of a heavy operator console in the horizontal plane, improving ergonomics while avoiding mechanical and safety-related problems arising from moving the operator console relative to a main unit of a scanner. The mechanism comprises four links and two bosses and is installed between the main unit of the ultrasound system and the operator panel, hidden below the latter. Seen from above, the four links resemble the back legs of a frog. The "frog-leg" configuration allows the operator to bring the operator panel up close by pulling it with one hand. The mechanism also allows a heavy CRT monitor to be mounted onto the operator panel and thus follow the latter's movement. When the system is to be moved, the operator panel is pushed back and locks into a compact "parked" position, allowing the handles on the operator panel to be used for moving the entire system.

23 Claims, 4 Drawing Sheets

MECHANISM FOR HORIZONTAL ADJUSTABILITY OF OPERATOR PANEL ON SCANNER

BACKGROUND OF THE INVENTION

This invention generally relates to equipment incorporating an operator panel. In particular, the invention relates to scanners having an operator panel and a display monitor.

Diagnostic imaging systems are ubiquitous in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Currently, a number of modalities exist for medical diagnostic imaging systems. These include computed tomography systems, x-ray systems (including both conventional and digital or digitized imaging systems), magnetic resonance systems, positron emission tomography systems, ultrasound systems, nuclear medicine systems, etc. In many instances, these modalities complement one another and offer the physician a range of techniques for imaging particular types of tissue, organs, physiological systems, etc. Health care institutions often arrange several such imaging systems at a single facility or at multiple facilities, permitting its physicians to draw upon such resources as required by particular patient needs.

Modern medical diagnostic imaging systems typically include circuitry for acquiring image data and for transforming the data into a useable form, which is then processed to create a reconstructed image of features of interest within the patient. The image data acquisition and processing circuitry is referred to as a "scanner", regardless of the modality, if physical or electronic scanning occurs as part of the imaging process. The particular components of the system and related circuitry, of course, differ greatly between modalities due to their different physics and data processing requirements.

Traditionally the position of the operator panel and monitor in a scanner has been a compromise between operators standing and sitting, tall and short operators, operators scanning left-handed or right-handed, operators scanning different parts of the body during one exam, and a need for making the system compact during in-hospital transport and storage. Premium scanners typically weigh between 150 and 240 kg. This makes such scanners difficult to position relative to the scanning bed, especially when the operator is sitting. Often examination rooms in hospitals are cramped and the scanner has to be moved each time a patient is entering or leaving the scanning bed. Also the operator has to adjust and move to find a good scanning position. When a good scanning position is found, the operator often has to stretch out to reach the operator panel, especially if the position of the operator panel is not adjustable relative to the main unit of the scanner.

Various commercially available scanners have adjustable operator panels. One such scanner has a top console which is horizontally adjustable through one two-link link. Another known scanner provides for height adjustment of the keyboard. Another scanner uses a split solution with keyboard and monitor mounted on respective single-link horizontally turnable links. The assignee of the instant application has models with height-adjustable keyboard and other models with telescopic height adjustment and single-link link horizontal adjustability.

There is a need for a scanner design having a horizontally adjustable operator panel with enhanced ergonomics to provide more comfortable working conditions for personnel and to prevent long-term load injuries arising from repetitive scanning. Such an adjustable operator panel should combine simple mechanics, compactness, symmetry, rigidity, freedom of movement, and avoidance of pinch points.

SUMMARY OF THE INVENTION

The present invention is directed to an articulated mechanism which achieves flexibility of a heavy operator console in the horizontal plane, improving ergonomics while avoiding mechanical and safety-related problems arising from moving the operator console relative to the main unit. The resulting horizontally adjustable operator panel has simple mechanics and freedom of movement, is compact, symmetric and rigid, and avoids pinch points.

In accordance with the preferred embodiment of the invention, the operator panel is adjustably mounted to the main unit of the equipment using an articulated mechanism comprising four links and two bosses. Although the preferred embodiment will be disclosed in the context of an ultrasound scanner, the invention has application in other types of scanners and, more generally, has application in other types of equipment incorporating an operator console.

The invention provides an ergonomically improved working position for system operators, such as operators of ultrasound scanners. In accordance with the preferred embodiment of the invention, the mechanism comprising four links and two bosses is installed between the main unit of the ultrasound system and the operator panel, hidden below the latter. Seen from above, the four links resemble the back legs of a frog. This mechanism allows quick and easy adjustment of the operator panel position in the horizontal plane relative to the main unit of the scanner. The "frog-leg" configuration allows the operator to bring the operator panel up close by pulling it with one hand. The mechanism also allows a heavy CRT monitor to be mounted onto the operator panel and thus follow the latter's movement. When the system is to be moved, the operator panel is pushed back and locks into a compact "parked" position, allowing the handles on the operator panel to be used for moving the entire system.

Other aspects of the invention are disclosed and claimed below.

DETAILED DESCRIPTION OF THE PREFERRED EMBODIMENTS

Figure 1:
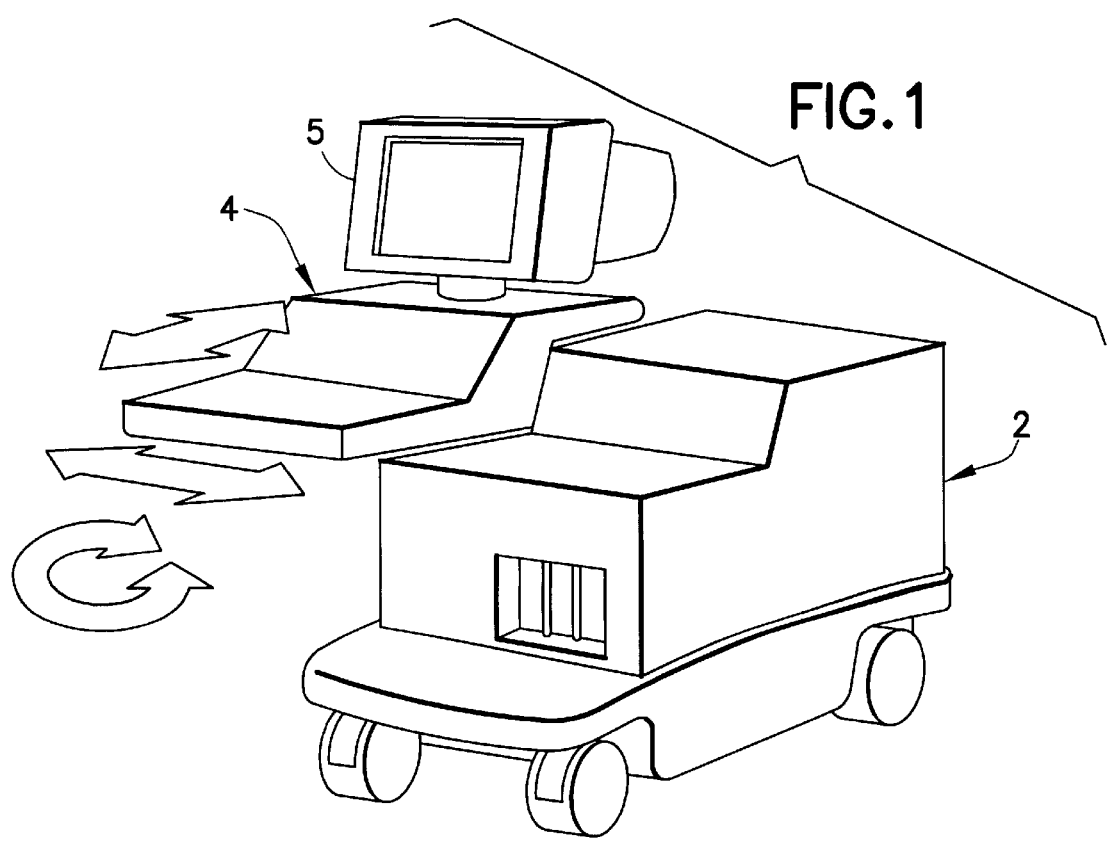
FIG. 1 is a drawing generally showing an ultrasound scanner in accordance with the preferred embodiment of the invention.

FIG. 1 shows an ultrasound scanner having a main unit 2 housing the majority of the scanner electronics and an operator console 4 movably mounted on the top of the main unit. In accordance with the preferred embodiment of the invention, the operator console 4 is mounted to the main unit 2 by means of the articulated mechanism shown in FIG. 2. Preferably, a display monitor 5 is mounted to the operator console 4. The degrees of freedom of the operator console 4 relative to the main unit 2 are indicated by arrows in FIG. 1. The operator console can be moved longitudinally forward and backward with or without rotation about a vertical axis or can be moved in a horizontal plane with longitudinal, lateral and rotational components.

Figure 2:
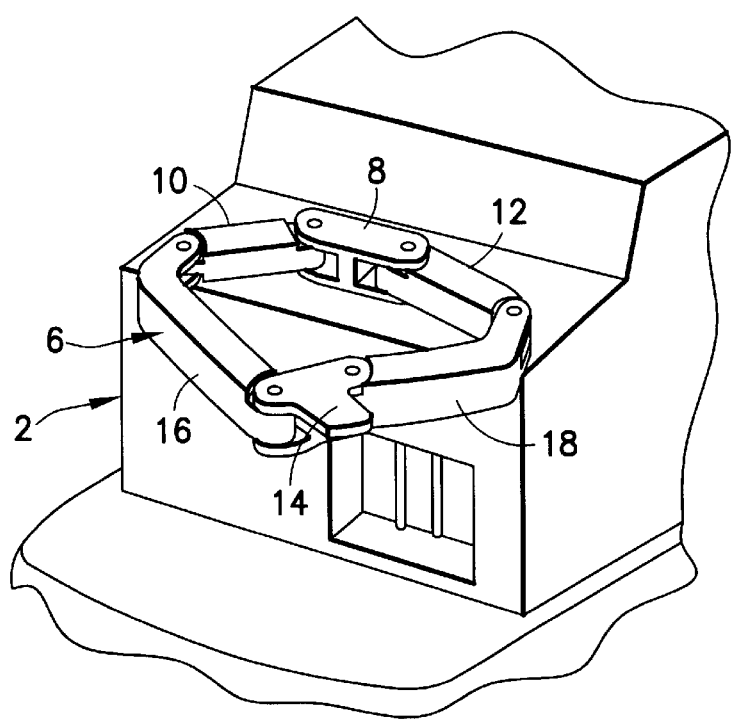
FIG. 2 is a drawing showing the mechanism in accordance with one preferred embodiment and its position relative to the rest of the ultrasound scanner.

The articulated mechanism 6 in accordance with the preferred embodiment of the invention and its position relative the rest of the system is shown in FIG. 2. The mechanism 6 is an assembly of jointed components. The mechanism comprises a rigid inner boss 8 that connects the mechanism to the main unit 2 either directly or via a mechanism for vertical adjustment (not shown). The components designated by numerals 10 and 12 are left and right rigid inner links respectively having one end pivotably coupled to the inner boss 8. The mechanism 6 further comprises a rigid outer boss 14 that connects the mechanism to the operator console 4. The components designated by numerals 16 and 18 are left and right rigid outer links respectively having one end pivotably coupled to the outer boss 14. The other end of outer link 16 is pivotably coupled to the other end of inner link 10, while the other end of outer link 18 is pivotably coupled to the other end of inner link 12. The outer links are preferably J-shaped. The inner and outer links 10 and 16 on the left side form one leg, while the inner and outer links 12 and 18 on the right side form another leg. All of the pivot points (there are six) have mutually parallel pivot axes which are perpendicular to the plane of movement.

Figure 3:
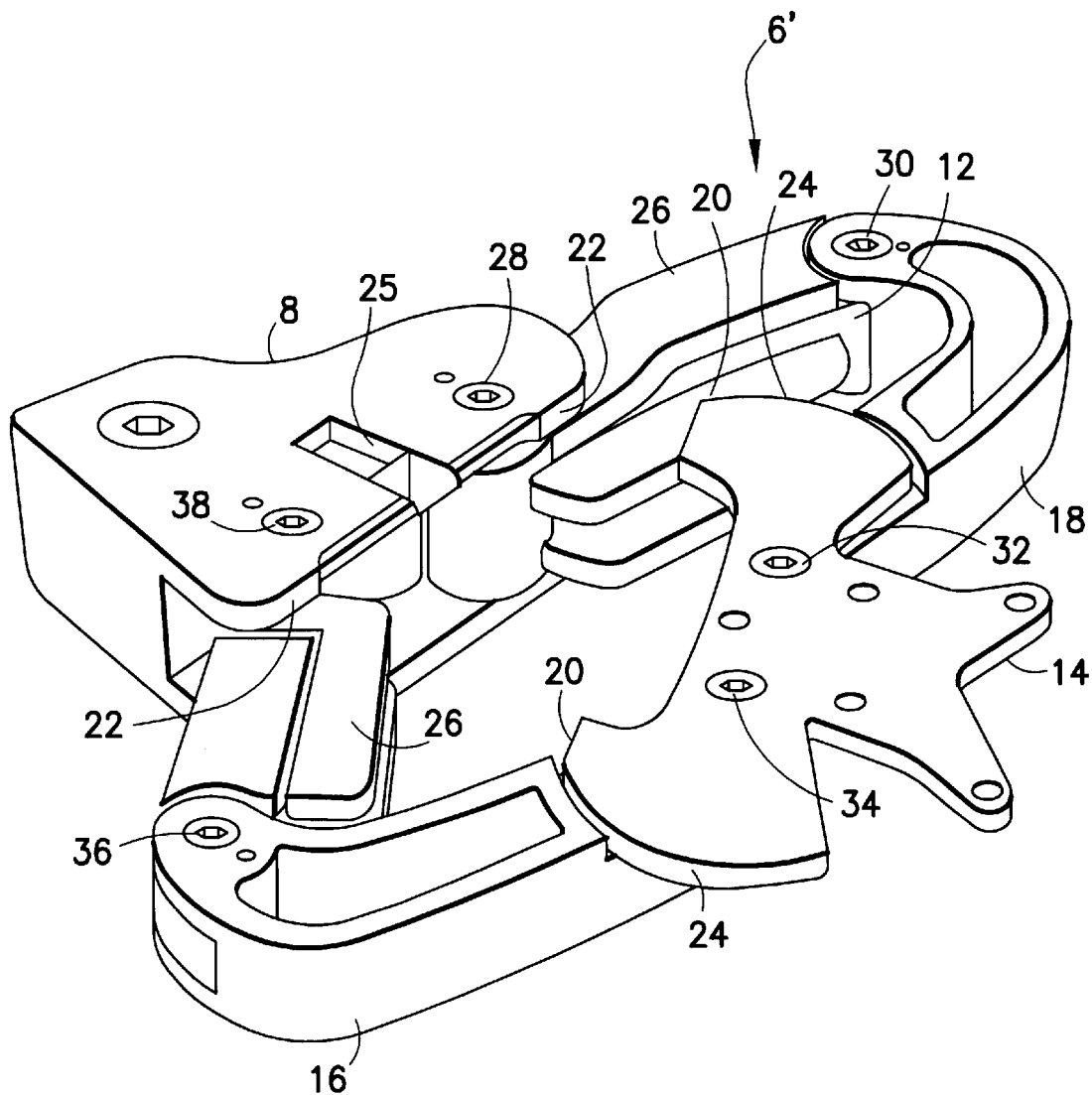
FIG. 3 is a drawing showing another preferred embodiment of the invention.

FIG. 3 shows in detail the structure of a mechanism 6' in accordance with another preferred embodiment of the invention. This mechanism was designed to avoid finger pinch points and to minimize build height. It also shows the fixed parts of the locking mechanism. The two "knobs" 20 on the outer boss 14' meets the inner boss 8' at the indicated surfaces 22. The curved sectors 24 provide finger pinching prevention by always filling the gaps in the outer links. A latch (not shown) positioned in the operator console (not shown in FIG. 3) hooks into the groove 25 in the inner boss 8' and holds the entire mechanism firmly locked (i.e., secures the outer boss relative to the inner boss) until released on the operator console. Soft rubber pads 26 with ribs cover the openings in the inner links and prevent finger pinching. FIG. 3 shows an inner boss 8' adapted to mounting on a vertical column somewhat offset from the center plane of the scanner. All parts except bolts, bearings and soft pads are preferably made out of cast aluminum.

Figure 4:
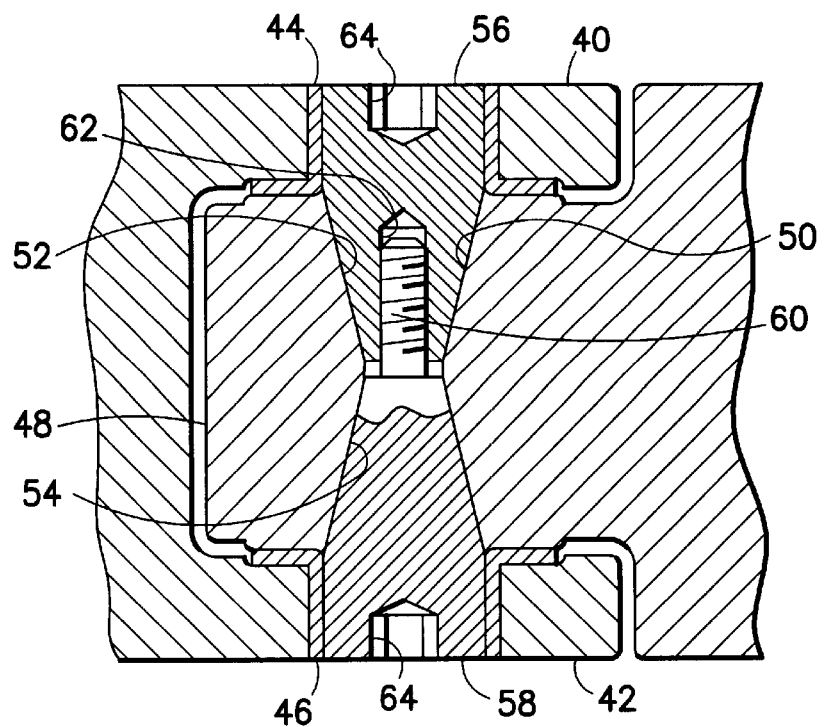
FIG. 4 is a drawing showing a cross-sectional view of one of the joints incorporated in the preferred embodiments of the invention.

The respective pivot points are designated by numerals 28, 30, 32, 34, 36 and 38 in FIG. 3. Each pivot point preferably comprises a joint having the principle of construction shown in FIG. 4. FIG. 4 depicts the joint for the pivot point 30 by which the right inner link 12 is pivotably coupled to right outer link 18. Pivot point 36 has an identical construction. The other pivot points, although not shown in detail, have a similar construction.

Referring to FIG. 4, the right outer link 18 has a clevis end formed in the shape of a U with holes in each end 40 and 42 for receiving respective upper and lower bearings 44 and 46. The right inner link 12 ends as a projection 48 of reduced height which is inserted between the ends 40 and 42 of the clevis and forms the center part of the joint. The annular flanges of the bearings 44 and 46 are disposed between the upper and lower surfaces of the projection 48 and the opposing surfaces of the clevis ends 40 and 42. The projection 48 has a vertical bore 50 which comprises an upper conical recess 52 which decreases in radius and a lower conical recess 54 which increases in radius in the downward direction, the conical recesses 52 and 54 being in communication and having the same radius in the middle of the projection 48. The maximum radius of conical recess 52 generally equals the inner radius of the upper bearing 44, while the maximum radius of conical recess 54 generally equals the inner radius of the lower bearing 46.

To assemble the joint, the conical recesses 52 and 54 are aligned with the openings in bearings 44 and 46, and then two conical hardened steels bolts 56 and 58 are respectively inserted as shown in FIG. 4. Bolt 56 comprises a circular cylindrical portion which sits inside the upper bearing 44 and a conical portion which sits inside the upper conical recess 52; bolt 58 comprises a circular cylindrical portion which sits inside the lower bearing 46 and a conical portion which sits inside the lower conical recess 54. In addition, bolt 58 has a threaded shaft 60 while bolt 56 has a threaded bore 62. The bolts 56 and 58 are coupled by screwing the threaded shaft 60 of bolt 58 into the threaded bore 62 of bolt 56. Preferably, each of the steel bolts 56 and 58 has a hexagonal recess 64 for fitting in tools used to tighten the bolts. The recess is sunk into the bolts so that it does not add to the total height, as an outwardly projecting hexagonal head would have done.

The coupled bolts form a pivot pin which pivots in the bearings 44 and 46 respectively installed in the clevis ends 40 and 42. By positioning the bearings 44 and 46 as far out as possible in the clevis part, strength is maximized for a given bearing size and height, while minimizing play. The tightened conical hardened steel bolts 56 and 58 ensure a firm, play-free connection to the projection 48.

Figure 5:
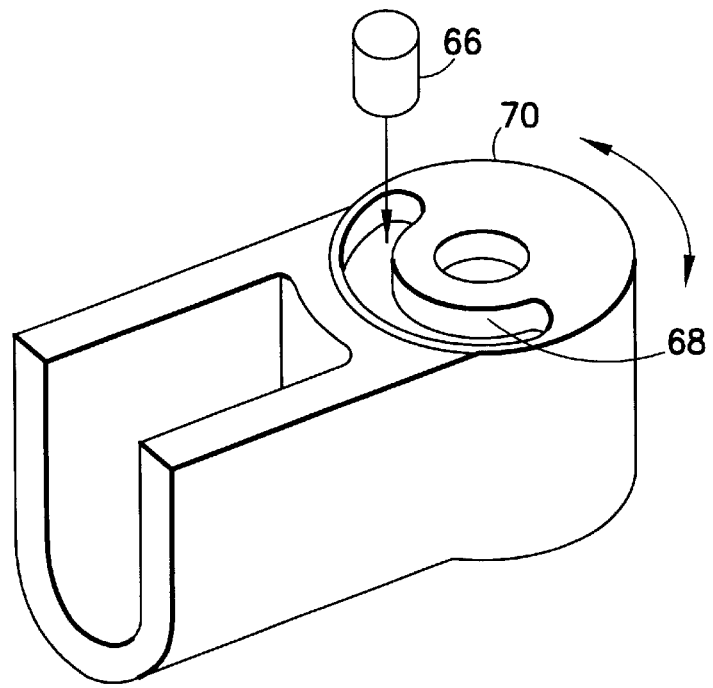
FIG. 5 is a drawing showing one of the stroke limiters incorporated in the preferred embodiments of the invention.

FIG. 5 shows the principle of the stroke limiters in accordance with the preferred embodiment of the invention. To avoid finger pinch points, the end stop surfaces have to be enclosed at all times. This is accomplished by having a steel pin 66 mounted to the clevis part (not shown in FIG. 5) of the joint which projects into a machined arcuate groove 68 in the center part 70 of the joint. By regulating the arc length of this groove 68, the stopping point of the different joints can be made with precision.

FIGS. 6–10 show the pattern of movement for the mechanism depicted in FIG. 2. The arrows indicate where end stops limit the stroke in different positions.

Figure 6:
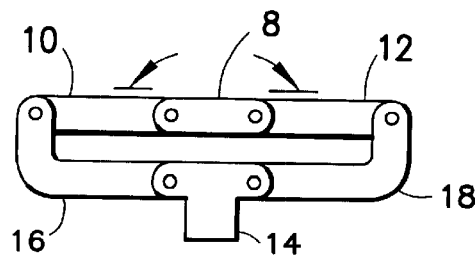
FIGS. 6–10 are a sequence of drawings showing the pattern of movement of the mechanism depicted in FIG. 2.

FIG. 6 shows the mechanism in parked, compacted position where end stops in the inner boss 8 prevent the inner links 10 and 12 from swinging further back.

Figure 7:
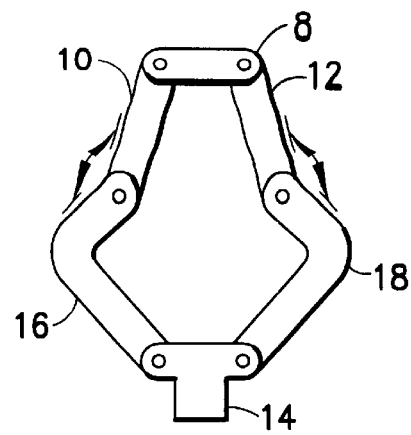

FIG. 7 shows the mechanism in the maximally extended position. As shown in FIG. 7, the end stops in the joints coupling the inner links 10, 12 to the outer links 16, 18 respectively prevent the links from eventually going "over the top", i.e., to a positional state where the operator console would be prevented from being pushed back. In other words, the end stops indicated in FIG. 7 prevent a state where the forwardly extended operator console cannot be pushed back. Comparing FIGS. 6 and 7, it can be seen that pivoting of each inner link is limited to a range which is less than 90 degrees.

Figure 8:
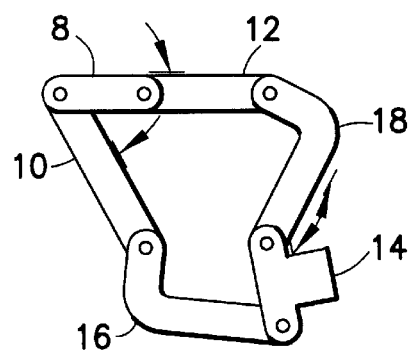

FIG. 8 shows the state of the mechanism when the console is pulled out and swung all the way to one side and rotated backwards. When the mechanism is in the position shown in FIG. 8, the top console is allowed to turn relative to the main unit because the center of gravity, especially with a CRT monitor, will lie towards the center of the system. Comparing FIGS. 7 and 8, it can be seen that rotation of the outer boss relative to the inner boss is limited to a range which is slightly more than 90 degrees in each direction.

Figure 9:
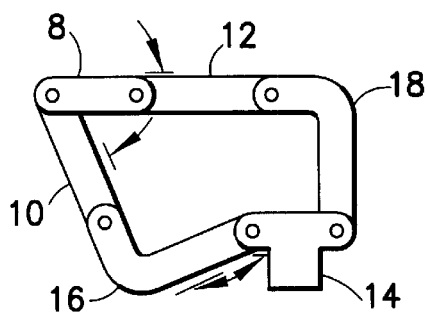

Referring now to FIG. 9, it can be seen that, in the horizontal position previously shown in FIG. 8, the outer boss 14 (and the operator console mounted thereto) is not allowed to rotate as much in the opposite direction. This would have caused stability issues because of the operator console's center of gravity being significantly offset relative to the outer boss 14.

Figure 10:
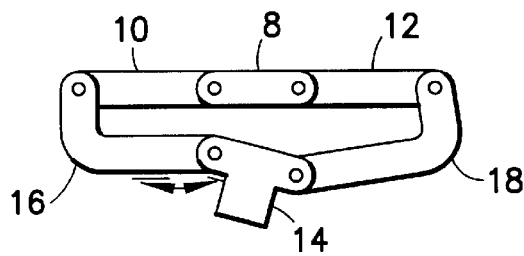

Finally, referring to FIG. 10, in the inner position the operator console is allowed to turn 15 degrees from side to side immediately after the lock has been disengaged.

The design in accordance with the preferred embodiment of the invention provides a high degree of quick and easy-to-use horizontal adjustability, thus dramatically improving the ergonomic qualities of the scanner as compared to conventional designs. The mechanism involves few moving parts and only rotational, plain bearings, the latter being cheaper and more robust than linear bearings. By initiating some movement of the top console, most bearings will experience some motion. Thus by having kinetic friction in most of the bearings, a shift in the direction of movement will not require extra effort to overcome static friction. The operator console will float freely in the plane without giving the operator the feeling of moving different joints and bearings one by one. Inherent in the mechanism are limitations in the different joints to prevent the operator console from being turned to unwanted angles. The angle the console is allowed to turn relative to the main unit changes as the console is moved from side to side. This function is very difficult to obtain by other mechanisms without using complex wire systems. The mechanism can also be built free of pinch points, without the need for surrounding it with bellows or covers. Compared to other mechanisms, the "frog leg" design of the preferred embodiment offers a wide movement, while being symmetric (avoiding tilt issues) and folding up to a very compact unit when parked. The design disclosed herein, together with the joint solution, offers a small building height for its strength. This is important for bringing the operator console ergonomically far enough down while maintaining accessible space underneath the console for peripherals. Combined with a center-wall spaceframe structure incorporating a sliding mechanism for vertical adjustment positioned in the center wall, the "frog leg" mechanism disclosed herein is particularly suited because it mounts to a point on or near the center plane of the system.

As used in the claims presented hereinafter, the term "boss" means a rigid support structure.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A system comprising an operator console, a main unit and a mechanism for mounting said operator console to said main unit to provide positional adjustment in a horizontal plane, wherein said mechanism comprises:

an inner boss secured to said main unit;

an outer boss secured to said operator console;

a first outer link pivotably coupled to said outer boss;

a second outer link pivotably coupled to said outer boss;

a first inner link pivotably coupled to said inner boss; and a second inner link pivotably coupled to said inner boss, wherein said first outer link is pivotably coupled to said first inner link and said second outer link is pivotably coupled to said second inner link, and the pivot axes of the pivotably coupled components being mutually parallel.

2. The system as recited in claim 1, wherein each of said first and second outer links is J-shaped.

3. The system as recited in claim 1, further comprising means for limiting the range of pivoting of said first outer link relative to said first inner link.

4. The system as recited in claim 1, further comprising means for limiting the range of pivoting of said first inner link relative to said inner boss.

5. The system as recited in claim 1, further comprising means for limiting the range of pivoting of said outer boss relative to said first outer link.

6. The system as recited in claim 1, wherein said inner boss comprises a recess for receiving a latch on said operator console.

7. The system as recited in claim 1, wherein in a parking state of said mechanism, first and second surfaces of said outer boss are in respective abutment with first and second surfaces of said inner boss.

8. The system as recited in claim 1, further comprising first and second soft pads which cover respective portions of said first and second inner links.

9. The system as recited in claim 1, wherein said outer boss comprises first and second curved sectors which fill gaps in said first and second outer links respectively throughout respective ranges of pivoting of said outer boss relative to said first and second outer links.

10. The system as recited in claim 1, wherein said main unit houses scanner electronics.

11. A system comprising an operator console, a main unit, and an articulated mechanism for mounting said operator console to said main unit to provide positional adjustment in a horizontal plane, wherein said articulated mechanism comprises:

an inner boss secured to said main unit;

an outer boss secured to said operator console;

a first articulated leg pivotably coupled at one end to said inner boss and at the other end to said outer boss; and a second articulated leg pivotably coupled at one end to said inner boss and at the other end to said outer boss.

12. The system as recited in claim 11, wherein said first articulated leg comprises a first outer link pivotably coupled to said outer boss and a second outer link pivotably coupled to said outer boss, while said second articulated leg comprises a first inner link pivotably coupled to said outer boss and a second inner link pivotably coupled to said outer boss, said first outer link being pivotably coupled to said first inner link and said second outer link being pivotably coupled to said second inner link, and the pivot axes of the pivotably coupled components being mutually parallel.

13. The system as recited in claim 11, wherein said inner boss comprises a recess for receiving a latch on said operator console.

14. The system as recited in claim 12, further comprising an arcuate groove formed in one of said first outer link and said first inner link and a pin which projects into said groove from the other of said first outer link and said first inner link.

15. The system as recited in claim 12, further comprising an arcuate groove formed in one of said inner boss and said first inner link and a pin which projects into said groove from the other of said inner boss and said first inner link.

16. The system as recited in claim 12, further comprising an arcuate groove formed in one of said first outer link and said outer boss and a pin which projects into said groove from the other of said first outer link and said outer boss.

17. The system as recited in claim 12, wherein said outer boss comprises first and second curved sectors which fill gaps in said first and second outer links respectively throughout respective ranges of pivoting of said outer boss relative to said first and second outer links.

18. The system as recited in claim 11, wherein said main unit houses scanner electronics.

19. The system as recited in claim 11, wherein rotation of said outer boss relative to said inner boss is limited to a range which is slightly more than 90 degrees in each direction.

20. The system as recited in claim 12, wherein rotation of each of said first and second inner links relative to said inner boss is limited to a range which is less than 90 degrees.

21. A system comprising an operator console, a main unit, and an articulated mechanism for mounting said operator console to said main unit to provide positional adjustment in a horizontal plane, wherein said articulated mechanism comprises a plurality of joints, at least one of said joints comprising first and second bearings which are coaxial, and first and second conical bolts being respectively seated in said first and second bearings, said first conical bolt comprising a threaded bore and said second conical bolt comprising a threaded shaft which is threadably coupled in said threaded bore.

22. The system as recited in claim 21, wherein each of said conical bolts has a respective recess for receiving a torquing tool.

23. The system as recited in claim 21, wherein said at least one joint comprises a clevis comprising first and second ends, said first and second bearings being respectively installed in said first and second ends of said clevis.

* * * * *